United States Patent [19]

Gerlach et al.

[11] Patent Number: 5,081,663
[45] Date of Patent: Jan. 14, 1992

[54] X-RAY APPARATUS WITH BEAM INDICATOR

[75] Inventors: Hans-Juergen Gerlach; Juergen Reimer, both of Erlangen, Fed. Rep. of Germany

[73] Assignee: Siemens Aktiengesellschaft, Munich, Fed. Rep. of Germany

[21] Appl. No.: 586,869

[22] Filed: Sep. 24, 1990

[30] Foreign Application Priority Data

Oct. 16, 1989 [EP] European Pat. Off. ......... 89119178.5

[51] Int. Cl.⁵ .............................................. G01D 18/00
[52] U.S. Cl. ..................................... 378/207; 378/162
[58] Field of Search .............. 378/207, 114, 117, 124, 378/140, 145, 162, 165–166

[56] References Cited

U.S. PATENT DOCUMENTS

| | | | |
|---|---|---|---|
| 3,581,094 | 5/1971 | Peyser et al. | 378/187 |
| 4,355,410 | 10/1982 | Sullins | 378/199 |
| 4,530,007 | 7/1985 | Schmidt . | |
| 4,918,714 | 4/1990 | Adamski et al. | 378/117 |

FOREIGN PATENT DOCUMENTS

| | | |
|---|---|---|
| 973069 | 4/1960 | Fed. Rep. of Germany . |
| 34393355 | 4/1986 | Fed. Rep. of Germany . |
| 2431239 | 2/1980 | France . |
| 2069129 | 8/1981 | United Kingdom . |

*Primary Examiner*—Janice A. Howell
*Assistant Examiner*—David P. Porta
*Attorney, Agent, or Firm*—Hill, Van Santen, Steadman & Simpson

[57] ABSTRACT

An x-ray apparatus including an x-ray source with a primary radiation diaphragm attached thereto has a luminescent foil disposed in the interior of either the x-ray source or the primary radiation diaphragm at a location so that the x-ray beam is incident thereon. Interaction of the luminescent foil with the x-ray beam causes the foil to emit light, which is conducted to an exterior of the apparatus by an optical waveguide. The light is therefore visible at a location at the exterior of the unit, such as in the housing, as a reliable indicator that x-rays are actually being generated.

7 Claims, 1 Drawing Sheet

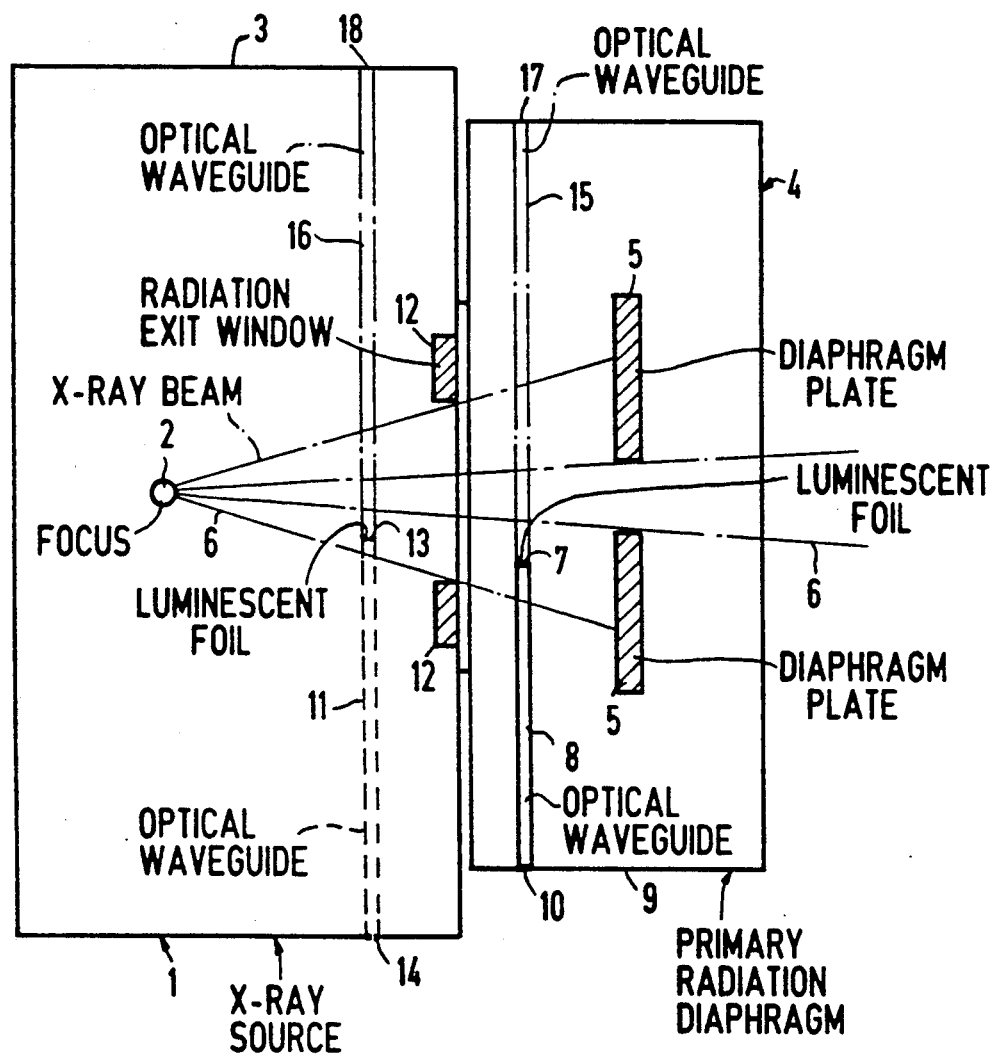

X-RAY APPARATUS WITH BEAM INDICATOR

BACKGROUND OF THE INVENTION

1. Field of the Invention

The present invention is directed to an indicator for providing visible identification in an x-ray apparatus when x-rays are actually being generated.

2. Description of the Prior Art

In x-ray devices it is known to provide an indicator or "telltale" lamp which is illuminated when the x-ray tube is energized for emitting x-rays. An incorrect display is possible, however, if, for example, due to a faulty contact the lamp is illuminated even though no radiation is present, or the lamp does not become illuminated even though radiation is present.

SUMMARY OF THE INVENTION

It is an object of the present invention to provide an indicator for the presence of an x-ray beam which provides an error-free display.

The above object is achieved in accordance with the principles of the present invention in an x-ray apparatus wherein a luminescent foil is located within the apparatus at a location so that the x-ray beam, when present, will be incident thereon. By interaction with the x-ray beam, the luminescent foil generates light, which is transmitted to an exterior of the apparatus by an optical waveguide. The outer end of the optical waveguide may project slightly from the apparatus housing, so that the presence of the x-ray beam can be visibly recognized. Since there are no electrical components or connections subject to failure or malfunctioning, an error-free indicator of the presence of the x-ray beam is achieved.

The luminescent foil and the optical waveguide may be arranged in the housing of the x-ray source, or may be arranged in the housing of the primary radiation diaphragm.

It is possible to provide a single optical waveguide and to transmit the light from the luminescent foil to a single location at the diaphragm housing or the x-ray source housing, however, it is also possible to transmit this light via a plurality of waveguides to various locations at the housings, so that a visible observation can be made at any position to determine whether x-rays are actually being generated.

In those installations wherein the x-ray generator (x-ray source combined with a primary radiation diaphragm) is covered by other components such that the x-ray generator is not easily visible, the optical waveguide can simply be extended to a location which is easily visible by an operator of the apparatus.

DESCRIPTION OF THE DRAWINGS

The single FIGURE is a side sectional view of an x-ray generator constructed in accordance with the principles of the present invention with the relevant internal components being schematically shown.

DESCRIPTION OF THE PREFERRED EMBODIMENTS

An x-ray generator consisting of an x-ray source 1 and a primary radiation diaphragm 4, attached thereto, is shown in the drawing. The x-ray source 1 has a housing 3, and the primary radiation diaphragm has a housing 9.

The x-ray source 1 has a focus 2 from which an x-ray beam 6 emanates. The beam 6 exits the housing 3 of the x-ray source 1 via a radiation exit window 12, and enters the housing 9 of the primary radiation diaphragm 4, wherein the beam 6 is limited in size by one or more diaphragm plates 5.

A luminescent foil 7 is disposed in the primary radiation diaphragm 4 at a location so that the x-ray beam 6 is incident thereon, but such that the luminescent foil 7 does not deteriorate the beam 6. The luminescent foil 7 may consist, for example, of the same material as is used for known intensifier foils in x-ray film cassettes. When the x-ray beam 6 is present, i.e. when x-rays are actually being generated, the luminescent foil 7 will interact with the x-rays and generate light. This light is conducted via an optical waveguide 8 to a visible location 10, such as at the exterior of the housing 9 of the primary radiation diaphragm 4. It will be understood that the visible location 10 may be disposed at any location which can be easily seen by an operator of the apparatus, and may even be disposed remote from the actual x-ray generator.

It is thus possible to monitor the presence of x-rays with a high degree of reliability, because it is the actual x-rays which are being used to generate the indicator light, rather than derived quantities such as, for example, the voltage at the x-ray tube.

Alternatively, or in addition, to the above-described indicator structure in the primary radiation diaphragm 4, a similar structure can be disposed in the x-ray source 1. For example, a luminescent foil 13 may be arranged in the housing 3 of the x-ray source 1, with the light generated thereby being conducted to a location 14 at an exterior of the housing 3 via an optical waveguide 11.

It is also possible to provide multiple optical waveguides, each being optically coupled to the luminescent foil 7 or the luminescent foil 13, so that light can be conducted to a plurality of exterior locations, so that indicators identifying the presence of the x-ray beam can be viewed from numerous locations around the apparatus. For example, a further waveguide 15 can be disposed in the primary radiation diaphragm 4 which conducts the light from the luminescent foil 7 to a further exterior location 17. Similarly a further optical waveguide 16 may be provided in the x-ray source 1 for conducting light from the luminescent foil 13 to a further exterior location 18. It will be understood that even further optical waveguides can be provided in any number of different orientations, and one or more of those waveguides may be extended to conduct the light to one or more locations remote from the generator.

Although further modifications and changes may be suggested by those skilled in the art, it is the intention of the inventors to embody within the patent warranted hereon all changes and modifications as resonably and properly come within the scope of their contribution to the art.

We claim as our invention:

1. An x-ray generator having a focus therein from which an x-ray beam emanates, a luminescent foil disposed in an interior of said x-ray generator for interacting with said x-ray beam to generate light, and an optical waveguide for conducting said light to a location at a visual exterior of said x-ray generator as an indicator to an operator that said x-ray beam is present.

2. An x-ray generator as claimed in claim 1 wherein said x-ray generator includes a primary radiation diaphragm having a diaphragm housing, and wherein said luminescent foil is disposed in said diaphragm housing and wherein said optical waveguide conducts said light from said luminescent foil to an exterior of said diaphragm housing.

3. An x-ray generator as claimed in claim 1 wherein said x-ray generator includes an x-ray source having an x-ray source housing, and wherein said luminescent foil is disposed in said x-ray source housing and wherein said optical waveguide conducts said light from said luminescent foil to an exterior of said x-ray source housing.

4. An x-ray generator as claimed in claim 1 further comprising at least one further optical waveguide optically coupled to said luminescent foil for conducting light from said luminescent foil to a further location at an exterior of said x-ray generator.

5. An x-ray generator as claimed in claim 1 further comprising at least one further luminescent foil and at least one further optical waveguide optically coupled to said further luminescent foil for conducting light from said further luminescent foil to a further location at an exterior of said x-ray generator.

6. An x-ray generator having a focus disposed in an interior of said x-ray generator from which an x-ray beam emanates, a luminescent foil disposed in the interior of said x-ray generator for interacting with said x-ray beam to generate light, and a plurality of optical waveguides optically coupled to said luminescent foil for conducting said light to a plurality of locations at an exterior of said x-ray generator as an indicator that said x-ray beam is present.

7. An x-ray generator having a focus disposed in an interior of said x-ray generator from which an x-ray beam emanates, a plurality of luminescent foils disposed in the interior of said x-ray generator for interacting with said x-ray beam to generate light, and a plurality of sets of optical waveguides, each set being respectively optically coupled to a luminescent foil for conducting light from the luminescent foil coupled thereto to a plurality of locations at an exterior of said x-ray generator as an indicator that said x-ray beam is present.

* * * * *